United States Patent [19]

Sakai et al.

[11] Patent Number: 5,224,478
[45] Date of Patent: Jul. 6, 1993

[54] REFLECTING-TYPE OXYMETER PROBE

[75] Inventors: Hiroshi Sakai, Komaki; Toshihiko Ogura, Inuyama; Satoshi Kohmura, Komaki, all of Japan

[73] Assignee: Colin Electronics Co., Ltd., Aichi, Japan

[21] Appl. No.: 932,741

[22] Filed: Aug. 25, 1992

Related U.S. Application Data

[63] Continuation of Ser. No. 615,401, Nov. 19, 1990, abandoned.

[30] Foreign Application Priority Data

Nov. 25, 1989 [JP] Japan .................. 1-136534[U]

[51] Int. Cl.5 .............................................. A61B 5/00
[52] U.S. Cl. ...................................... 128/633; 128/666; 356/41
[58] Field of Search .................. 128/633-664-666; 356/41

[56] References Cited

U.S. PATENT DOCUMENTS

| | | | |
|---|---|---|---|
| 724,913 | 4/1903 | Montgomery | 604/278 |
| 3,810,460 | 5/1974 | Van Nie | 128/666 |
| 4,564,023 | 1/1986 | Hess | 128/785 |
| 4,669,488 | 7/1987 | Hess | 128/785 |
| 4,685,464 | 8/1987 | Goldberger et al. | 128/666 |
| 4,825,872 | 5/1989 | Tan et al. | 128/633 |
| 4,825,879 | 5/1989 | Tan et al. | |
| 4,830,014 | 5/1989 | Goodman et al. | |
| 4,859,057 | 8/1989 | Taylor et al. | 128/633 |
| 4,860,768 | 8/1989 | Hon et al. | |
| 4,880,304 | 11/1989 | Jaeb et al. | |
| 4,915,116 | 4/1990 | Hasebe | 128/666 |
| 4,971,062 | 11/1990 | Hasebe | 128/666 |
| 5,080,098 | 1/1992 | Willett et al. | 128/633 |

FOREIGN PATENT DOCUMENTS 53-26437 8/1978 Japan .

*Primary Examiner*—Lee S. Cohen
*Assistant Examiner*—Robert L. Nasser, Jr.
*Attorney, Agent, or Firm*—Oliff & Berridge

[57] ABSTRACT

A probe for a reflection-type oxymeter which measures a blood oxygen saturation of a subject, the probe including a light emit device emitting at least two lights having different wavelengths toward a body portion of the subject, a light detect device detecting the lights reflected by the body portion of the subject, a housing supporting the light emit and detect devices, and an elastic member secured to the housing, the elastic member including an adhesive portion, the adhesive portion being spaced from the body portion of the subject with the housing contacting the body portion, the adhesive portion being elastically deformed and adhered to the body portion so that the housing is pressed against the body portion with a pressing force within a predetermined range due to an elastic return force of the deformed adhesive portion.

7 Claims, 2 Drawing Sheets

REFLECTING-TYPE OXYMETER PROBE

This is a continuation of application Ser. No. 07/615,401 filed Nov. 19, 1990, now abandoned.

BACKGROUND OF THE INVENTION

1. Field of the Invention

The present invention relates to a probe for an oxymeter of the reflection type which measures a blood oxygen saturation of a subject based on lights which are reflected from skin of the subject, and more particularly to such a probe which is adapted to be set on the skin.

2. Related Art Statement

There is known a probe for a reflection-type oxymeter which measures a blood oxygen saturation of a subject, which probe includes (a) light emitting means for emitting two lights having different wavelengths toward skin of the subject, (b) light detecting means for detecting the lights reflected from the skin, and (c) a housing accommodating the light emitting and detecting means. For example, such a probe is disclosed in U.S. Pat. No. 4,880,304. The prior art probe is set on the skin with, for example, a pressure sensitive adhesive tape being applied over both the housing and the skin.

The light emitting means of the above indicated reflection-type oxymeter emits an infra-red light and a red light having different wavelengths, toward the skin, and the light detecting means detects the lights reflected from the capillary bed in the hypodermis lying under the epidermis. The oxymeter determines a blood oxygen saturation of the subject based on the amplitudes of intensities of the lights detected by the light detecting means, according to a predetermined relationship (formulae). However, since the prior art probe is set on the skin by being pressed against the skin with an adhesive tape being applied over both the housing and the skin, the pressing force applied to the probe or housing may largely vary in different cases, thereby deteriorating the reliability or accuracy of blood oxygen saturation measurement. As clearly shown in the graph of FIG. 3, the intensity of a light reflected from the skin of a subject varies depending upon the pressing force applied to the housing or skin. The prior art probe suffers from the problem that the pressing force applied to the housing for setting the housing on the skin of the subject, largely varies because of the application of an adhesive tape over both the housing and the skin and therefore does not always fall within a suitable range. In the case where the pressing force applied to the probe exceeds the upper limit of the suitable range or does not reach the lower limit of the range, the light reflected from the skin shows an insufficient intensity to be utilized for determining a blood oxygen saturation.

SUMMARY OF THE INVENTION

It is therefore an object of the present invention to provide a probe for an oxymeter of the reflection type which probe assures reliable measurement of blood oxygen saturation.

The above object has been achieved by the present invention, which provides a probe for a reflection-type oxymeter which measures a blood oxygen saturation of a subject, the probe comprising light (a) emit means for emitting at least two lights having different wavelengths toward a body portion of the subject, (b) light detect means for detecting the lights reflected by the body portion of the subject, (c) a housing supporting the light emit and detect means, and (d) an elastic member secured to the housing, the elastic member including an adhesive portion, the adhesive portion being spaced from the body portion of the subject with the housing contacting the body portion, the adhesive portion being elastically deformed and adhered to the body portion so that the housing is pressed against the body portion with a pressing force within a predetermined range due to an elastic return force of the deformed adhesive portion.

In the probe constructed as described above, the adhesive portion of the elastic member is deformed and adhered to the skin of a subject, so that the probe is set on the skin of the subject such that the housing is pressed against the skin with a suitable pressing force due to an elastic return force of the deformed adhesive portion. Therefore, every user can set the probe on the skin of a subject with a pressing force within a suitable pressing force range. In contrast to the previously identified prior art probe which is set on the skin of a subject by applying an adhesive tape over both the housing and the skin, the pressing force applied to the housing of the present probe does not excessively largely change, namely, reliably falls within a predetermined suitable range. Thus, the present probe assures that the light reflected from the skin of the subject has a sufficient intensity and accordingly that the measurement of blood oxygen saturation is made with high accuracy.

According to a feature of the present invention, the elastic member has a generally annular shape and is secured at a radially inner edge thereof to an outer surface of the housing, the elastic member including a deformable outer peripheral portion, the adhesive portion comprising the outer peripheral portion and a pressure sensitive double coated adhesive sheet applied to the outer peripheral portion. The generally annular elastic member may have a plurality of notches which extend from a radially outer edge thereof through the outer peripheral portion toward the radially inner edge thereof.

According to another feature of the present invention, the housing is pressed against the body portion with the pressing force falling within a range of 80 to 190 g/cm². The pressing force more suitably falls within a range of 100 to 155 g/cm².

According to yet another feature of the present invention, the elastic member includes a central portion in which the housing is fitted, and a deformable outer peripheral portion, the adhesive portion comprising the outer peripheral portion and a pressure sensitive double coated adhesive sheet applied to the outer peripheral portion.

According to a further feature of the present invention, the elastic member is formed of silicone rubber.

BRIEF DESCRIPTION OF THE DRAWINGS

The above and optional objects, features and advantages of the present invention will be better understood by reading the following detailed description of the presently preferred embodiments of the invention when considered in connection with the accompanying drawings in which.

DETAILED DESCRIPTION OF THE PREFERRED EMBODIMENTS

Figure 1:
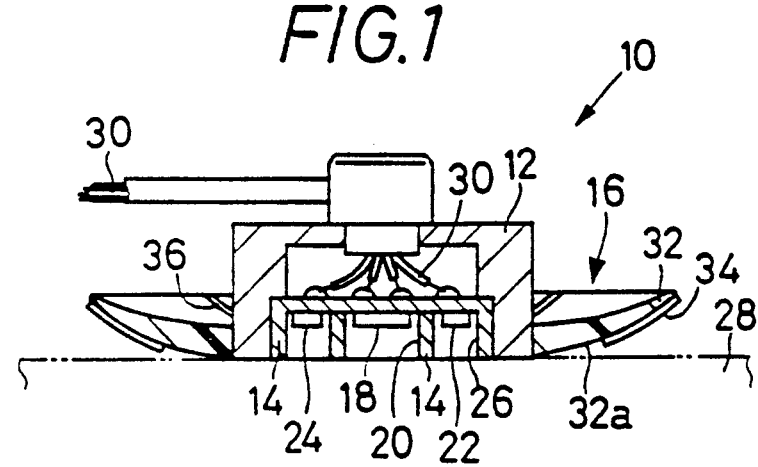
FIG. 1 is a cross sectional view of an embodiment of the probe of the present invention.

Referring first to FIG. 1, there is shown a probe 10 for a pulse oxymeter of the reflection type. The probe 10 includes a cylindrical housing 12 with a bottom wall, a shade member 14 fitted in an opening of the housing 12, and a generally annular elastic flange member 16 adhered to an outer circumferential surface of the housing 12. The shade member 14 includes a central recess 20 accommodating a light detecting element 18, and a peripheral annular recess 26 accommodating a first and a second light emitting element 22, 24 which emit an infra-red light and a red light having different wavelengths toward a skin 28 of a subject, respectively. The light detecting element 18 detects the infra-red and red lights reflected from the capillary bed of the skin 28, and generates first and second signals representative of the intensities of the infra-red and red lights, respectively. With the probe 10 contacting the skin 28, the shade member 14 prevents the lights reflected at the outer surface of the skin 28 from being incident to the light detecting element 18, and also prevents ambient (natural and/or artificial) light from being incident to the light detecting element 18. The light detecting element 18 and first and second light emitting elements 22, 24 are coupled to a main device (not shown) of the pulse oxymeter via respective conductor members 30. The main device includes a drive device for periodically and alternately activating the first and second light emitting elements 22, 24 to light, and a control device for discriminating the first and second signals produced by the light detecting element 18, from each other, in synchronism with the periodic and alternate activations of the first and second light emitting elements 22, 24. The main device of the pulse oxymeter determines a blood oxygen saturation of the subject based on amplitudes of the first and second signals, namely, the infra-red and red lights reflected from the skin 28, according to a well-known algorithm as disclosed in Japanese Patent Application laid-open for opposition purpose under Publication No. 53-26437 or U.S. patent application Ser. No. 07/531,768.

The elastic flange member 16 is formed of a silicone rubber, for example. As shown in FIG. 1, the flange member 16 has a deformable peripheral portion 32 which warps upward in a radially outer peripheral portion thereof like a dish. Therefore, with the probe 10 contacting the skin 28, the peripheral portion 32 is spaced apart from the skin 28 such that a radially outer edge of the peripheral portion 32 is the most distant from the skin 28. A lower surface 32a of the peripheral portion 32 opposed to the skin 28 is provided with a pressure sensitive double coated adhesive sheet 34. The adhesive sheet 34 is adhered at one side thereof to the lower surface 32a of the peripheral portion 32 by being pressed by the user, and is adhered at the other side thereof to the skin 28 by the user pressing on the peripheral portion 32. Thus, the peripheral portion 32 serves as an adhesive portion of the elastic member 16.

Figure 2:
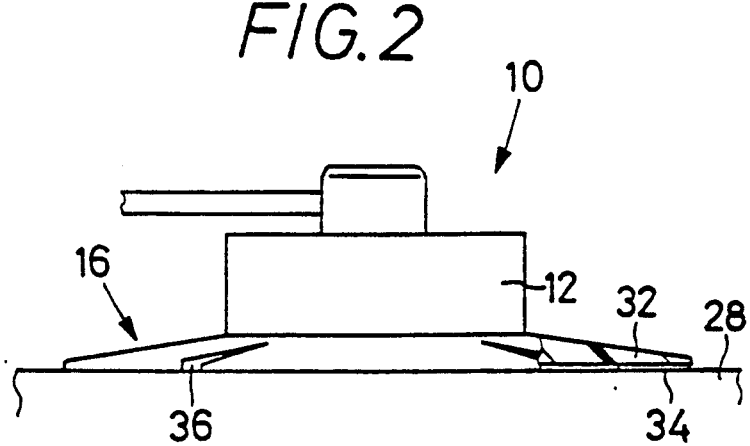
FIG. 2 is a view of the probe of FIG. 1 set on the skin of a subject, with an adhesive portion thereof being deformed.

FIG. 2 shows the adhesive portion 32 deformed and adhered to the skin 28 with the adhesive sheet 34 being adhered to the skin 28. More specifically, the adhesive portion 32 is elastically deformed by a user such as a nurse or a patient, so as to be adhered to the skin 28. With the elastic member 16 being adhered to the skin 28, the housing 12 is pressed against the skin 28 with a pressing force falling within a suitable pressing force range. The pressing force results from an elastic return force of the deformed adhesive portion 32. In other words, the elastic member 16 has an appropriate elasticity that assures that the housing 12 is pressed with the suitable pressing force.

Figure 3:
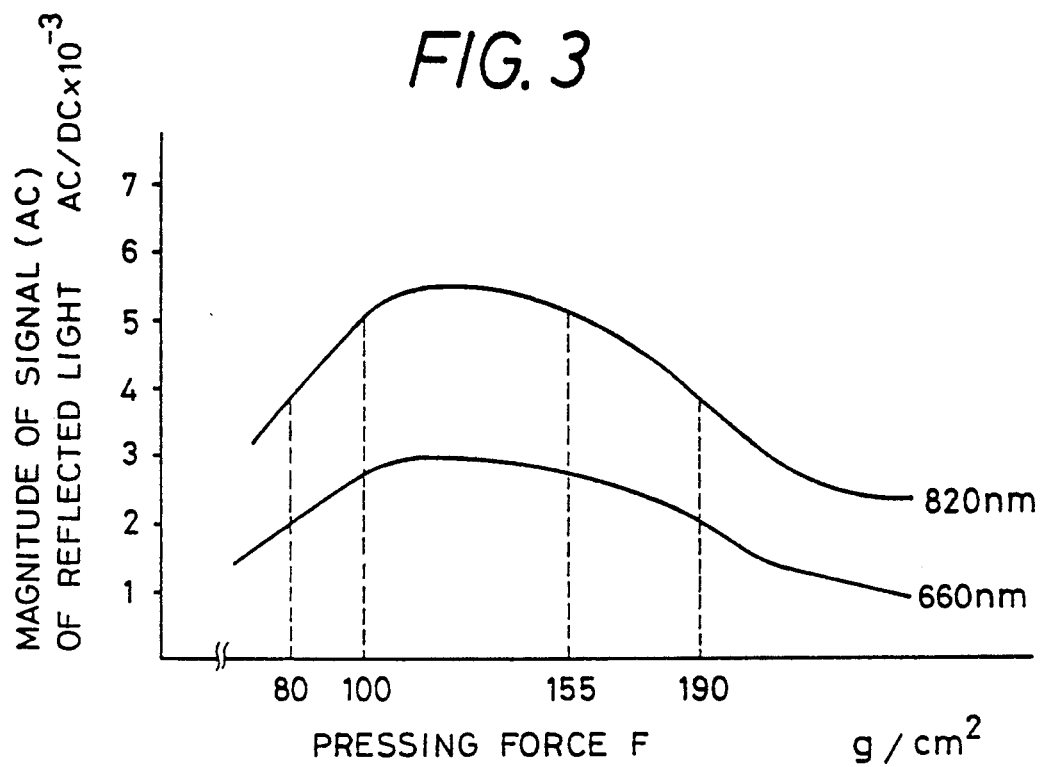
FIG. 3 is a graph showing a relationship between pressing force applied to a housing of the probe of FIG. 1 and magnitude of signal representative of a light reflected from skin of a subject.

The graph of FIG. 3 shows a relationship between pressing force, F, applied to the housing 12 and magnitude of the first and second signals corresponding to the infra-red (820 nm) and red (660 nm) lights. More specifically, the signal magnitude is obtained by multiplying by $10^3$ a ratio of the magnitude of the alternating component (AC) of the first or second signal to the magnitude of the direct component (DC) of the same signal. It is preferred that pressing force F fall within the range of 80 to 190 g/cm$^2$, and more suitably within the range of 100 to 155 g/cm$^2$. The elastic member 16 has a plurality of radial notches 36 which extend radially inward from an outer circumference or radially outer edge thereof through the adhesive portion 32. The radial notches 36 serve for avoiding an elastic return force of the deformed adhesive portion 32 from being produced in a circumferential direction of the adhesive portion 32. The elastic flange member 16 has a thickness which decreases in a direction from the inner peripheral edge thereof toward the peripheral adhesive portion 32.

As is apparent from the foregoing description, the oxymeter probe 10 is set on the skin 28 simply by deforming and adhering to the skin 28 the adhesive portion 32 of the elastic member 16. Consequently, the present probe 10 is fixed on the skin 28 such that the housing 12 is pressed against the skin 28 with a pressing force corresponding to an elastic return force of the deformed adhesive portion 32. Therefore, the housing 12 or probe 10 is pressed against the skin 28 with a suitable pressing force falling within an intended or desired pressing force range, irrespective of high or low skill of the user. In addition, the variation of the pressing force applied to the housing 12 is extremely reduced, as compared with that of the prior art probe which is set on the skin of a subject by applying an adhesive tape over both a housing of the probe and the skin. Thus, the present probe 10 assures that the light detecting element 18 produces the first and second signals having sufficiently great magnitudes and therefore that the pulse oxymeter determines a blood oxygen saturation of the subject with satisfactory accuracy by utilizing those signals.

Figure 4:
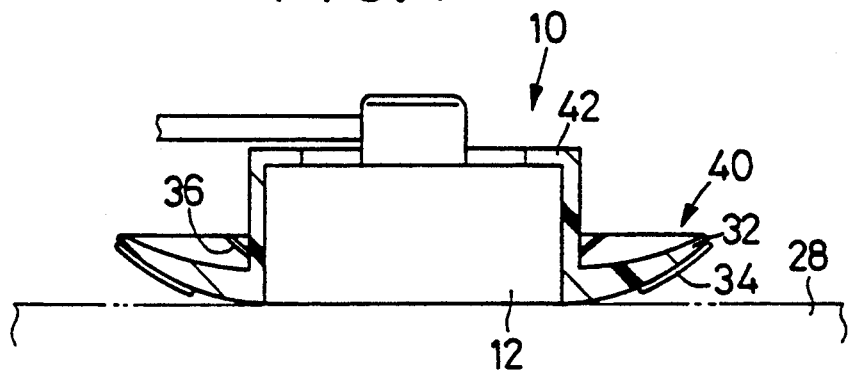
FIG. 4 is a cross sectional view of another embodiment of the present invention before being set.

Referring next to FIG. 4, there is shown another embodiment of the present invention. The same reference numerals as used in FIG. 1 are used for designating corresponding members or parts of the embodiment of FIG. 4.

In FIG. 4, reference numeral 40 designates an elastic member 40 including a cylindrical portion 42 having a configuration permitting a cylindrical housing 12 to be fitted therein. With the cylindrical housing 12 fitted in the cylindrical portion 42 of the elastic member 40, an adhesive portion 32 of the elastic member 40 is deformed and adhered to a skin 28 of a subject, whereby a probe 10 for a pulse oxymeter of the reflection type is set on the skin 10 such that the housing 12 is pressed against the skin 28 with a pressing force corresponding to an elastic return force of the deformed adhesive portion 32. Therefore, the present embodiment provides the same advantages as those of the embodiment of FIG. 1. In addition, since the elastic member 40 is secured to the housing 12 such that the housing 12 is fitted in the cylindrical portion 42 of the elastic member 40, it is very simple to replace the elastic member 40 by a new one for another subject.

It is to be understood that the present invention by no means is limited to the illustrated embodiments but may be embodied with various changes.

For example, it is possible to use three or more light emitting elements emitting three or more lights having different wavelengths, for improving the accuracy of blood oxygen saturation measurement, in place of the first and second light emitting elements 22, 24 used in the illustrated embodiments.

Further, it is possible to use a rectangular housing and/or a rectangular elastic member, in place of the cylindrical housing 12 and/or annular elastic member 16, 40 used in the illustrated embodiments.

In addition, it is possible to use, in place of the annular elastic member 16, 40 consisting of a single member, an elastic member consisting of a plurality of separate portions which are secured to the housing such that those portions are spaced apart from each other around the housing 12.

Furthermore, it is possible to apply a double coated adhesive sheet to both an upper surface of the adhesive portion 32 opposite to the lower surface 32a, and the skin 28, in place of applying the adhesive sheet 34 to the lower surface 32a.

The elastic member 16, 40 may be formed of other appropriate materials such as a plastic material.

It is to be understood that the present invention may be embodied with other changes, modifications and improvements that may occur to those skilled in the art without departing from the spirit and scope of the invention as defined in the appended claims.

What is claimed is:

1. A probe for a reflection-type oxymeter which measures a blood oxygen saturation of a subject, the probe comprising:

light emit means for emitting at least two lights having different wavelengths toward a body portion of said subject;

light detect means for detecting the lights emitted from said light emit means and reflected by said body portion of said subject;

a housing supporting said light emit means and said light detect means; and an elastic member secured to said housing, said elastic member including a generally annular portion and being engaged at an inner peripheral edge of said annular portion with an outer surface of said housing, said annular portion including an outer peripheral adhesive portion, said adhesive portion being spaced from said body portion of said subject when said housing is in contact with said body portion, said adhesive portion being elastically deformable and thereby adherable to said body portion so that said housing is pressed against said body portion with a pressing force within a predetermined range due to an elastic return force of the deformed adhesive portion adhered to said body portion, said annular portion having a thickness which decreases in a direction from said inner peripheral edge thereof toward said outer peripheral adhesive portion thereof.

2. The probe as set forth in claim 1, wherein said outer peripheral adhesive portion comprising a double coated adhesive sheet.

3. The probe as set forth in claim 1, wherein said generally annular portion of said elastic member has a plurality of notches which extend from an outer peripheral edge thereof through said outer peripheral adhesive portion toward said inner peripheral edge thereof, each said notch connecting between opposite surfaces of said annular portion.

4. The probe as set forth in claim 1, wherein said deformed outer peripheral adhesive portion of said elastic member comprises means for producing said pressing force, said pressing force falling within a range of 80 to 190 g/cm$^2$.

5. The probe as set forth in claim 1, wherein said deformed outer peripheral adhesive portion of said elastic member comprises means for producing said pressing force, said pressing force falling within a range of 100 to 155 g/cm$^2$.

6. The probe as set forth in claim 1, wherein said elastic member includes a central portion in which said housing is fitted and which is integral with said outer peripheral adhesive portion, said adhesive portion comprising a double coated adhesive sheet.

7. The probe as set forth in claim 1, wherein said elastic member is formed of silicone rubber.

* * * * *